US010149938B2

(12) United States Patent
Murphy et al.

(10) Patent No.: US 10,149,938 B2
(45) **Date of Patent: *Dec. 11, 2018**

(54) DISTRIBUTED MEDICATION DELIVERY METHOD HAVING AUTONOMOUS DELIVERY DEVICE

(71) Applicant: Renaudia Medical, LLC, San Diego, CA (US)

(72) Inventors: William H. Murphy, San Diego, CA (US); Richard H. Salzar, Carlsbad, CA (US)

(73) Assignee: Renaudia Medical, LLC, San Diego, CA (US)

( * ) Notice: Subject to any disclaimer, the term of this patent is extended or adjusted under 35 U.S.C. 154(b) by 597 days.

This patent is subject to a terminal disclaimer.

(21) Appl. No.: 14/808,928

(22) Filed: Jul. 24, 2015

(65) Prior Publication Data

US 2016/0015894 A1 Jan. 21, 2016

Related U.S. Application Data

(62) Division of application No. 13/528,758, filed on Jun. 20, 2012, now Pat. No. 9,089,642.

(Continued)

(51) Int. Cl.

*A61M 31/00* (2006.01)
*A61M 5/172* (2006.01)

(Continued)

(52) U.S. Cl.

CPC ............ *A61M 5/1723* (2013.01); *A61M 5/00* (2013.01); *A61M 5/172* (2013.01); *G06F 3/0488* (2013.01);

(Continued)

(58) Field of Classification Search

CPC ............... G06F 19/3469; G06F 19/326; G06F 19/3462; G06F 19/3468; G06F 3/0488; G06F 19/3412; G06F 19/3437; A61M 2205/50; A61M 5/172; A61M 2005/14208; A61M 2205/502; A61M 2205/505;

(Continued)

(56) References Cited

U.S. PATENT DOCUMENTS 4,696,671 A 9/1987 Epstein et al.
4,756,706 A 7/1988 Kerns et al.

(Continued)

*Primary Examiner* — Jason Flick
(74) *Attorney, Agent, or Firm* — Thomas A. Runk; Brooks Kushman P.C.

(57) ABSTRACT

A method for delivering medication includes programming an operations processor of a medication delivery operations module to control the base function of medication delivery of a delivery device at a selectable rate and a selectable volume. An advanced medication delivery program is created by an advanced program processor that is part of an advanced interface module ("AIM") located with the operations module in the same housing, although the processors are separate. When the advanced delivery program is complete and in a buffer, the operations processor executes the stored advanced delivery program under which the operations processor automatically varies at least one of the rate of delivery and volume of delivery values in accordance with the advanced delivery program autonomously without being under real time control of, or dependent on, any remote processor or data source, including the AIM. Support for PK applications is provided.

20 Claims, 7 Drawing Sheets

180 182 198 196 188
DRUG: PROPOFOL
VTBI MAX 50 mL
RATE MAX 5.0 mL/HR
EXTERNAL PROCESSOR AND MEMORY
206 84 33 204 184
PUMP OPERATIONS MODULE
202 200
194 PATIENT POPULATION: ADULT
min 0 mL
min 0.5 mL/HR
186
192 DRUG LIBRARIES
190 PATIENT POPULATION PARAMETERS

Related U.S. Application Data

(60) Provisional application No. 61/499,091, filed on Jun. 20, 2011.

(51) Int. Cl.

| | |
|---|---|
| ***A61M 5/00*** | (2006.01) |
| ***G06F 19/00*** | (2018.01) |
| ***G06F 3/0488*** | (2013.01) |
| ***G16H 40/40*** | (2018.01) |
| ***G16H 50/50*** | (2018.01) |
| *A61M 5/142* | (2006.01) |
| *A61M 5/14* | (2006.01) |

(52) U.S. Cl.

CPC ........ *G06F 19/326* (2013.01); *G06F 19/3462* (2013.01); *G06F 19/3468* (2013.01); *G16H 40/40* (2018.01); *G16H 50/50* (2018.01); *A61M 5/1408* (2013.01); *A61M 5/14228* (2013.01); *A61M 2205/50* (2013.01); *A61M 2205/502* (2013.01); *A61M 2205/505* (2013.01); *A61M 2205/52* (2013.01); *F04C 2270/0421* (2013.01)

(58) Field of Classification Search

CPC .. A61M 2205/52; A61M 5/00; A61M 5/1408; A61M 5/14228; A61M 5/1723; F04C 2270/0421; G16H 40/40; G16H 50/50

USPC .. 604/65–67, 131, 151, 890.1, 891.1, 93.01, 604/95.01, 503

See application file for complete search history.

(56) References Cited

U.S. PATENT DOCUMENTS

| | | | |
|---|---|---|---|
| 5,010,473 | A | 4/1991 | Jacobs et al. |
| 5,041,086 | A | 8/1991 | Koenig et al. |
| 5,429,602 | A | 7/1995 | Hauser |
| 5,522,798 | A | 6/1996 | Johnson et al. |
| 5,681,285 | A | 10/1997 | Ford et al. |
| 5,713,856 | A | 2/1998 | Eggers et al. |
| 5,772,635 | A | 6/1998 | Dastur et al. |
| 5,814,015 | A | 9/1998 | Gargano et al. |
| 5,935,099 | A | 8/1999 | Peterson et al. |
| 6,083,206 | A | 7/2000 | Molko |
| 6,270,478 | B1 | 8/2001 | Mernoe et al. |
| 6,631,291 | B2 | 10/2003 | Viertio-Oja et al. |
| 6,699,230 | B2 | 3/2004 | Jaafar et al. |
| 6,761,895 | B2 | 7/2004 | Sawada et al. |
| 7,347,836 | B2 | 3/2008 | Peterson et al. |
| 7,556,036 | B2 | 7/2009 | Bouillon et al. |
| 7,645,258 | B2 | 1/2010 | White et al. |
| RE41,291 | E | 4/2010 | Viertio-Oja et al. |
| 2006/0064053 | A1 | 3/2006 | Bollish et al. |
| 2007/0179434 | A1 | 8/2007 | Weinert et al. |
| 2007/0233520 | A1 | 10/2007 | Wehba et al. |
| 2009/0177188 | A1 | 7/2009 | Steinkogler |
| 2010/0185181 | A1 | 7/2010 | Alme et al. |

38
42
44
40
50
46
20
48
22
60
62
58
46
24
48
26
50
28
52
51
49
47
30
53
32
34
36

DISTRIBUTED MEDICATION DELIVERY METHOD HAVING AUTONOMOUS DELIVERY DEVICE

CROSS-REFERENCES TO RELATED APPLICATIONS

This application is a divisional of prior application Ser. No. 13/528,758, filed Jun. 20, 2012, which claims the benefit of U.S. Provisional Application No. 61/499,091, filed Jun. 20, 2011, which is incorporated by reference herein.

BACKGROUND

The invention relates to control over medical delivery devices and more particularly, to medical delivery systems and methods having safety-enhancing configurations designed to lessen the effects of processor control errors.

Infusion pumps are in widespread use in the medical field. Numerous types of infusion pumps and infusion pump systems are known in the art. Infusion pumps have been designed with the base functions of a delivery rate and a volume-to-be-infused ("VTBI") (or delivery time and total dose). Over the years as processors have evolved with increased capability, faster speeds, and reduced cost, infusion pumps, as well as many other medical devices that deliver medical treatment to patients, have incorporated these processors and have become more complex with many more features made available. Very complex medication delivery profiles can be programmed into such pumps for the care and treatment of patients. Doctors, nurses, and technicians who are trained to program and use the complex features are often referred to as "super users." Such super users are able to program such pumps with very complex fluid delivery programs, and in some cases, configure them for specific use in particular wards of hospitals or other healthcare institutions.

Many of these advanced infusion pumps may be used in different pumping modes as the infusion pump may include several embedded programs to enable different operational modes. In the environment of intensive care units, cardiac care units, operating rooms, or trauma centers, it is often necessary to infuse into the patient one to eight different drugs simultaneously. In addition, some of the drugs used in these environments are not directly compatible with each other and therefore need to be infused into the patient at different points of the body. Such multiple infusions at different patient delivery sites require different pumping "channels" or pumping modules. In addition, it is frequently necessary to observe and recall the condition of the patient at certain intervals or to adjust the medication in accordance with the patient's reaction to it. To do so, changes to the pumping program of one channel may need to be made without disturbing drug delivery or device operation of other channels. In addition, in order to be able to recall patient conditions, large amounts of patient data must be stored and access to and manipulation of that data must be made available without disturbing any ongoing pumping processes.

In some cases, a modular programmable patient care system is used that comprises an apparatus for centrally interfacing with a plurality of connected functional devices that provide patient medication infusions and patient monitoring. The number of pumping modules, the complexity of the infusion programs that can be applied for each one, each program of which may differ from the others, and the number and complexity of patient monitors can generate a large amount of data for a central controller to process, and in some cases, can cause data programming and monitoring overloads. Even with single channel devices, the complexity of monitoring and controlling the device has created a time management issue when the user interface is added to the activities being controlled and responded to by the processor. Adding multiple channels just increases the probability of time management issues.

Such systems containing multiple infusion pumping devices are known in the medical field and are a natural response to the need for multiple pumps on a single patient. For example, U.S. Pat. No. 4,756,706 to Kerns et al. discloses a centrally-managed infusion pump system in which pump and monitoring modules are attached to a central management unit (CMU) or central controller. The central management unit controls the internal setup and programming of each of the attached pump modules, and receives and displays information from them.

U.S. Pat. No. 4,898,578 to Rubalcaba, Jr. also discloses a medication infusion system that includes a plurality of infusion pump modules that may selectively be attached to a central management unit or central controller (CMU) so as to provide for centralized control. In particular, the CMU obtains infusion parameters from the user and then performs calculations with the parameters to establish the desired infusion rate at a designated attached pump module. Once this rate is determined, the central management unit controls the infusion accordingly.

Turning now to FIG. 1, there is shown an existing medication delivery system 20 comprising a central management unit 22 (CMU), three infusion pumps 24, 26, and 28, and an oximeter 30, all of which are connected with and controlled by the CMU. All of the infusion pumps and the oximeter are connected with the same patient 32 in this example. All the foregoing devices 22, 24, 26, 28, and 30 are mounted to a floor stand 34 having a stable base 36. Also mounted to the floor stand at its top is a medication hanger 38 from which three medication containers are hung 40, 42, and 44. The right-most container 40 is connected with the top pump 24 and the patient 32 through a fluid line 46, with the pump controllably delivering the fluid of the container 40 to a first delivery site 47 at the patient. The middle container 42 is connected with the center pump 26 and the patient 32 at a different location, or delivery site 49, than the top pump through a fluid line 48, with the pump controllably delivering the fluid of the container to the patient. The left-most container is connected with the bottom pump 28 and the patient 32 through a fluid line 50 with the pump controllably delivering the fluid of the container to yet another delivery site 51 on the patient. The oximeter 30 receives oximetry data from a sensor (not shown), located at the patient at a location 53, selected so at to sense the necessary patient physiology, through a data line 52 for processing.

The CMU of FIG. 1 includes a user interface 58 comprising a display 60 and a keypad 62. The CMU receives programming input through its interface 58 and provides real-time programming control over each of the pumps or channels 24, 26, and 28. The CMU provides instructions to each of the pumps in real time to which they are responsive, it monitors the functional operation of each pump, and it monitors the operating timers of each pump and its respective processor. The CMU stores a drug library that is used both as a safety feature and a data base. The CMU monitors the delivery of each pump and updates instructions in real time to each pump according to programming of the CMU and possibly in accordance with oximeter data. The CMU also responds to user data entry to update instructions to one or more of the pumps. The pumps are responsive in real time to the updated instructions; i.e., they are under the direct control of the CMU. The CMU may or may not be connected with a remote processor, such as a pharmacy server, or an administration server central to a healthcare facility.

In the centralized control systems discussed above, there are several disadvantages. For example, in these systems the central management unit must be aware of and must control much of the functionality of the attached pump units. This can result in a large data processing load for the CMU. Some systems include a single complex central management unit (CMU) that must be used to control and program multiple infusion pumps. Complex central management units having a high data processing load are undesirable in clinical situations due to the possibility that a data overload may occur in which the processor is unable to timely process all data and output instructions. In such a situation, the CMU typically shuts down and consequently, all pump modules are shut down since they are under the direct control of the CMU. Shutdowns of the CMU and its pump modules can occur unpredictably with the result that the patient does not receive the medication at the desired time unless the system can be reset and restarted immediately or a replacement system can be located and programmed immediately. The same shutdown can happen in a single-channel pump where the processor becomes overwhelmed by complex programming and data processing requests.

Medication errors, that is errors that occur in the ordering, dispensing, and administration of medications, regardless of whether those errors cause injury or not, are a significant consideration in the delivery of healthcare in the institutional setting. The Sep. 9, 2002 issue of Archives of Internal Medicine reported a study indicating that nearly one in every five doses of medicine given to patients in the typical hospital is a medication error ("Medication Errors Observed in Thirty-Six Health Care Facilities"). This study confirms the findings from earlier reports, including the 1999 Institute of Medicine Report, which revealed that more than 50,000 deaths in the United States annually are the result of medication errors. Medication errors are the eighth leading cause of death in the United States. Additionally, adverse drug events ("ADE") defined as injuries involving a drug that require medical intervention, which are a subset of medication errors, represent some of the most serious medication errors, and are responsible for a number of patient injuries and death.

Healthcare facilities continually search for ways to reduce the occurrence and severity of medication errors. Various systems and methods have been considered and developed at present to reduce the frequency of occurrence and severity of preventable adverse drug events ("PADE") and other medication errors.

Manufacturers have tried using various techniques to avoid infusion errors, one of which includes the use of hand-held personal digital assistants ("PDA") that are designed to provide drug administration scheduling, drug administration verification, and the electronic documentation of drug administration. These devices are predominantly used to verify the administration of oral, intramuscular ("IM"), subcutaneous, and topical drugs and have limited capability in verifying the administration of intravenous ("IV") drugs. PDAs have been found to be useful for scheduling and perhaps monitoring, but can do very little or nothing about data overload and shutdown of an infusion pump system.

Healthcare facilities continuously strive to provide quality patient care and many steps have been taken to lessen the chances of such errors occurring. The possibility of medical errors, such as where the wrong patient receives the wrong drug at the wrong time, in the wrong dosage, or even where the wrong surgery is performed, are a significant concern for all healthcare facilities. Various solutions to these problems have been proposed, such as systems that use bar codes or RFID tags to identify patients and medications, or systems allowing the beside entry of patient data. While these systems also have advanced the art significantly, infusion data processing and programming errors continue to be a problem. For example, even where the medication order includes the correct infusion parameters and those parameters are correctly entered into an infusion pump, a data overload of the pump's processor or a remote centralized processor may cause the pump to stop administering the medication to the patient, thus causing a delivery error to the patient.

As briefly mentioned above, very complex pumping programs can be generated in the care and treatment of patients. The ability to control automatically a pump to provide a complex medical delivery regimen or pattern can have a significant benefit for a patient. A medication delivery pattern can be designed to optimize delivery of a particular medication that takes into account factors of the particular situation. Costs are lowered since the attention of nurses is not required each time a delivery parameter of the pump must be changed—it is done automatically. Although conventional drug infusion controllers have greatly improved the efficiency and ease with which medications are delivered to a patient, complex pumping programs, and the data produced from them, can reach the limits of certain processors. Data overloads are possible and their occurrence is not predictable. In some areas of medication delivery, even higher levels of data and instruction processing are necessary. The processor is "highly" taxed and when multiple requests are made of the device, changing delivery parameters occur, complex algorithms are running, single fault failure timing is in place, etc., devices on the market are shutting down without alarm conditions in some instances. The issue is the defined frequency of monitoring and control interface with the pump while also needing to recognize and respond to the user interface.

For example, certain pharmacokinetic models can require very complex infusion programs. U.S. Pat. No. 5,010,473 to Jacobs discloses a model-based open-loop process for controlling the concentration of a drug delivered intravenously to a patient as a function of the rate of infusion. A three-compartment pharmacokinetic (PK) model is used to determine the plasma drug concentration. Such PK systems are attractive for certain therapy, but require a large amount of programming, data manipulation, and control. Based upon the linear relationship between data pairs comprising a rate of infusion and a corresponding plasma drug concentration, an interpolated rate is determined by a microprocessor as a function of the specified plasma drug concentration. The actual infusion rate of the drug during successive time intervals is repetitively used to compute the plasma drug concentration at the end of each time interval. For each iteration, state variables from the previous computation are applied to determine the next interpolated infusion rate. Open-loop medication delivery control methods can achieve the specified plasma drug concentration, but a relatively complex medication delivery program is incorporated.

It will be apparent that controlling the administration of a plurality of drugs through a multi-channel drug infusion system using a PK model to predict the drug concentration and control the rate of infusion would require significant programming tasks over the prior art control of a single channel. If desired, a different PK model could then be selectively applied to control the delivery of each different drug through each channel of a multi-channel drug delivery system, or the same model could be used for the control of each channel of the system.

At times, a physician may find it necessary to alter briefly the parameters of a drug therapy. If the drug administration is being controlled by a PK model, the physician may want to switch to a manual mode for a period of time, for example, to administer a bolus dose. It should thereafter be possible to switch back to the PK model controlled mode. Accordingly, it is important that the control for a pump that is used to administer drugs in accordance with a PK model be able to track the history of the drug administered and take into consideration changes that occur while the PK model controlled mode is interrupted by a manual controlled mode, when the PK model control mode resumes. Since the history of the blood plasma concentration must be retained to achieve this goal, the infusion system control should be able to display both historical and predicted blood plasma and compartment effect drug concentrations levels to medical personnel for each drug administered, during either model controlled or manual controlled modes of operation. The model should continue to track and display these parameters, even after the drug infusion has stopped, so long as the patient's case is active. If all the above is performed by an infusion pump, or by a system of pumps with a central controller, significant data processing loads can occur for the processor or processors involved. Should such data loads exceed the processor's capability, a shut-down may occur and the therapy could be delayed.

It has been recognized that infusion pump designs currently on the market present potential safety issues. This may best be demonstrated by the fact that the U.S. Food and Drug Administration ("FDA") issued a proposed Infusion Pump Improvement Initiative on Apr. 22, 2010. Their justification for the initiative is that the number of recalls and potentially understated number of safety events involving infusion pumps are too high.

Observations:

The following observations are made after a review of FDA Medical Device Reports ("MDRs"), details provided with infusion pump recalls, and assessment of human factors known to exist in health care facilities.

During pump operation, software, hardware, and the user interface make major contributions to reported causes of pump recalls.

A. The intravenous (IV) infusion pump hardware/software interface uses a master/slave model where the master process controller, or "master processor," is the master for multiple channels. The master/slave relationship mandates that the pump channel operate only when the master control module or processor is functioning properly. This master/slave model can result in conflicts between the master processor's need to perform specific system checks and the user's demand for the master processor to process instructions being provided by the user. The processor as the master requires that the pump performance be interrupted if a processor or control module failure occurs.

B. To clarify the above problem through a comparison to another high data load system, video game programmers are faced with the same problem in that as the console game program begins to utilize too high a percentage of the processor's capacity, the "super user" begins to see slight delays in the video updates (for example, characters begin to freeze in place on the screen). The same is true with IV infusion pumps. The exception is that with the IV pump, the super user sees an error code or a potential programming error. The significant number of recalls associated with this design approach has been used as part of the FDA Infusion Pump Improvement Initiative Complexities of pump programming are not supported with the user interface screens provided with the feature-enhanced infusion pumps currently on the market.

Numerical keypads have a similar data entry error rate regardless of the style of keypad used. This added with the human factor of confirmation bias (humans tend to fail to check closely when asked to confirm) results in some level of over- or under-infusion of the solution (drug).

The advanced infusion pumps provide the users with the ability to program the pumps to address many different therapeutic procedures. However, the same feature enhancements require the user to program the pump while advancing through a series of screens. Each screen may use the same key as previously used for a different purpose. The potential errors associated with multiple functions for the same key potentially increase the error rates experienced as practitioners move from one patient population to another.

Infusion pumps are designed to address all of the needs in the healthcare facility; i.e., they have the ability to pump a wide range of volumes. This increases the pump's ability to deliver significantly more fluids than reasonably logical to neonatal patients and also allows deliveries so small that the delivery rates are not clinically significant for large adult patients.

The infusion pumps do not support easy readability during operation. This is especially true when multiple channels are operating and an error condition is detected. Alarms sound and delivery stops or is affected as a result of the error conditions. This condition is further complicated when the practitioner attempts to clear the error condition at the CMU and incorrectly takes action on channels not affected by the error condition.

No infusion pump currently on the market known to the inventors was designed to address the specific needs of anesthesia.

No infusion pump currently on the market addresses the specific needs of the neonatal intensive care patient population. Specifically, the drug dilution of many drugs being delivered at the same time may actually require the neonatal patient to receive more total fluids than is therapeutically beneficial to the patient.

Hence those skilled in the art have recognized a need for safer medication delivery devices. A need has also been recognized for a medical delivery device that is not susceptible to terminating delivery of a medication in the event that a remote processor that is controlling delivery ceases functioning properly. An additional need has been recognized for a medical device that is capable of receiving and operating under a complex medication delivery program. Another need has been recognized for safer data input devices and methods so that fewer mistakes are made when inputting data related to medication delivery. The invention fulfills these needs and others.

SUMMARY OF THE INVENTION

Briefly, and in general terms, the present invention is directed to a medical delivery device having a base delivery function with the capability to run advanced delivery programs autonomously.

In particular, there is provided a system for the delivery of medication, the system comprising a medical delivery operations module having a base function of medication delivery, the medical delivery operations module comprising a delivery mechanism, a user interface, a buffer memory, a communications system, an operations module processor, and a base function control program stored in a non-volatile memory that is configured to program the medical delivery operations module for the base function, wherein the communications system is configured to receive an advanced medication delivery program from a source outside the medical delivery operations module and store the advanced program in the buffer memory, and wherein the operations module processor is programmed to access the buffer memory and when the advanced medication delivery program has been completely loaded into the buffer, to execute the advanced medication delivery program autonomously.

In accordance with more detailed aspects, the operation module processor is further programmed to override execution of an executing advanced medication delivery program by receiving a STOP signal from the user interface. The advanced medication delivery program stored in the buffer memory comprises a sequence of varying base function operations that may be performed one at a time, with the operations module processor being programmed to access the buffer memory to retrieve a base function operation after an earlier one has been executed.

In yet further aspects, the medication delivery system further comprises an advanced interface module ("AIM") configured to create advanced medication delivery programs, the AIM comprising an input device, a display, a medication delivery library containing delivery parameters and acceptable values for medications, and an AIM processor configured to prepare an advanced medication delivery program including varying base functions.

In other detailed aspects, the display of the AIM includes a graphical touch screen, wherein the AIM processor is further programmed to display an acceptable range of values for a selected medication on the touch screen and accept a touch of a user to select a particular value in the range. The graphical touch screen displays slide controls for parameters related to an accessed delivery parameter from the medication library, and receives movement of a cursor within the slide control to select a value for the medication. The advanced interface module is located in a housing that is separate from the medication delivery operations module, although in another aspect, the advanced interface module is located in a housing that also contains the medication delivery operations module.

In more aspects in accordance with the invention, the operations processor is programmed to ignore control data from outside the medication delivery operations module when the operations processor is executing an advanced program.

In method aspects in accordance with the invention, there is provided a method for the delivery of medication, the method comprising programming a processor of a medication delivery operations module to perform a base function of the operations module, programming the operations module processor to check a buffer memory for the existence of a complete advanced medication delivery program, upon finding a complete advanced medication delivery program existing in the buffer, executing the advanced delivery program on the delivery operations module autonomously, and ignoring control signals received from an external source during the execution of the advanced delivery program.

In more detailed method aspects, the method further comprises overriding execution of an advanced medication delivery program upon receiving a STOP signal from a user interface of the operations module. The method further comprises preparing an advanced medication delivery program in an advanced interface module that is separate from the operations module, wherein preparing the advanced program comprises assembling a sequence of varying base function operations.

In yet other detailed method aspects, the delivery method further comprises displaying a graphical image of a range of values from which an operator may select a value for preparing the advanced program. The displayed range of values is retrieved from a library of acceptable values for a particular medication. The medical delivery method also comprises the step of displaying a cursor within the range of acceptable values, and programming the cursor to be movable to a selected position within the acceptable range by the touch of a user.

These and other advantages of the invention will become apparent from the following more detailed description when taken in conjunction with the accompanying drawings of illustrative embodiments.

DETAILED DESCRIPTION OF THE PREFERRED EMBODIMENTS

Figure 1:
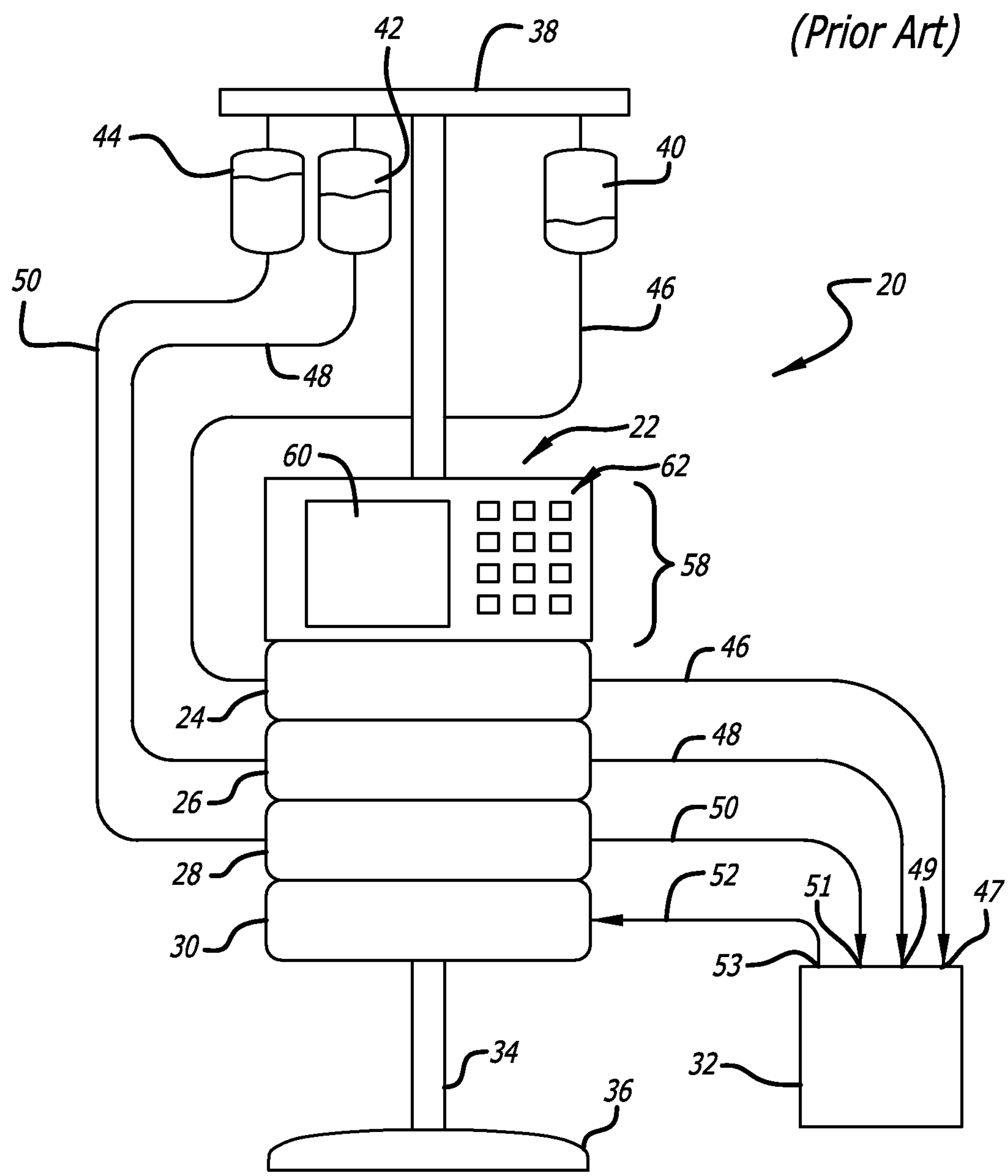
FIG. 1 is a view of a prior fluid delivery and patient monitoring system in which a central management unit (CMU) controls the operation of a plurality of medical devices, three of which are infusion pumps and one of which is a patient physiological parameter monitor (oximeter), and receives data from all four, the CMU also having a user interface including a keypad that allows control and data inputs for programming each device, and having a display to view the performance of each controlled device and data produced by each.
Figure 2:
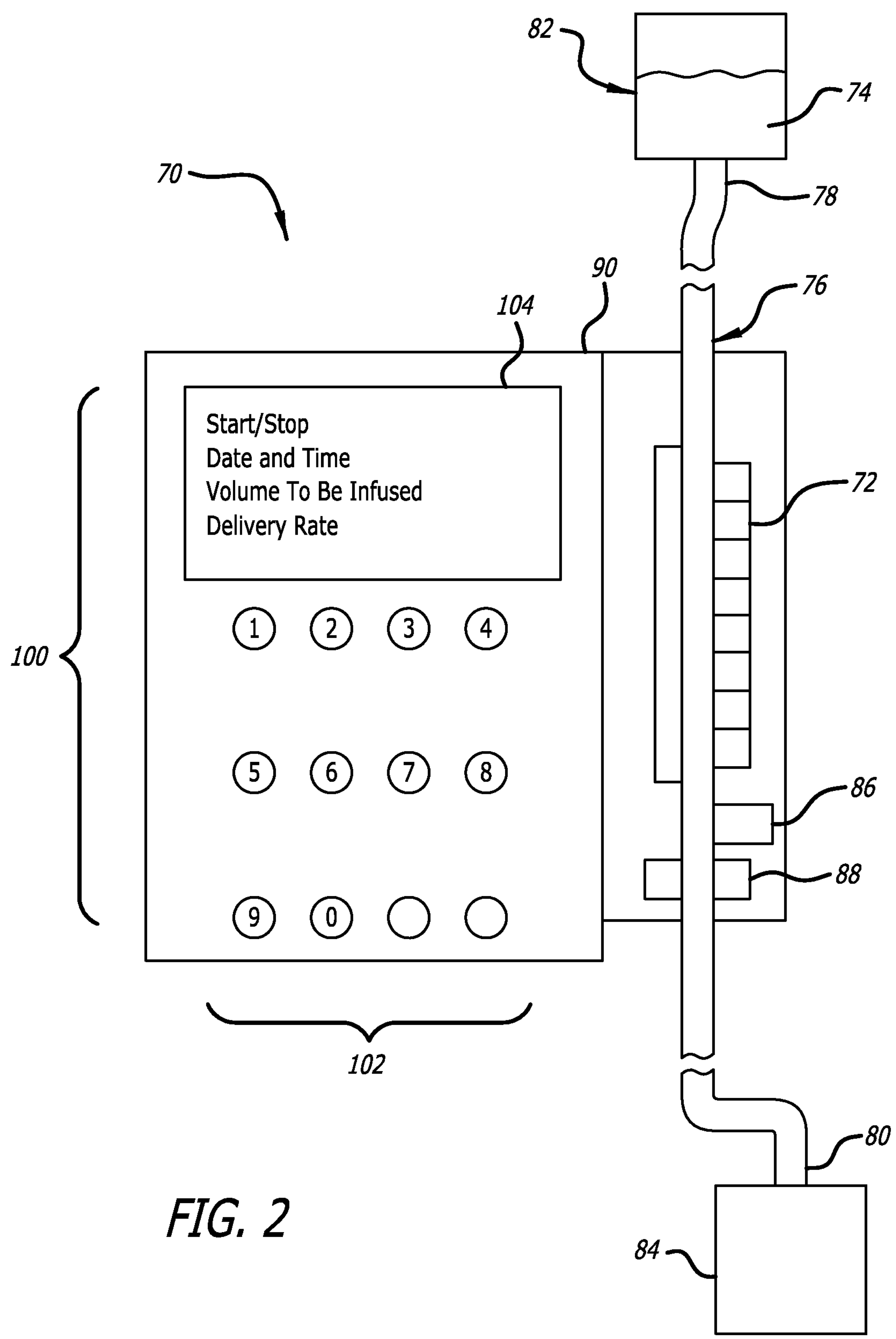
FIG. 2 is an exemplary infusion pump system shown operating on a delivery tube to move medical fluid from a container to a patient, the pump system having a touch-screen interface that permits control and data entry and displays data, a keypad input device, a peristaltic pumping mechanism, and sensors in this embodiment.

Referring now in further detail to the drawings in which like reference numerals are used to refer to like or corresponding elements among the several figures, there is generally shown in FIG. 2 an infusion pump system 70. In particular, the pump system includes a peristaltic pump mechanism 72 for moving fluid 74 through a delivery tube 76 from an upstream end 78 of the tube to a downstream end 80. In this case, the delivery tube 76 interconnects a fluid container 82 with a patient 84. The base function of the infusion pump system 70 is to move controllably a certain amount of the fluid (volume to be infused or "VTBI") from the container to the patient. The pump system 70 may also include additional safety features that may or may not be mandated by governmental regulatory agencies. In this case, a pressure sensor 86 and an air-in-line sensor 88 are included.

The pressure sensor and air-in-line sensor are not shown or described herein in any further detail since such devices are well known to those of ordinary skill in the art. Similarly, the peristaltic mechanism is not shown or described in any further detail since it likewise is well known to those of ordinary skill in the art. Other safety devices may be required beyond those shown here, and other pumping mechanisms may be used to move the fluid from the container to the patient; a peristaltic mechanism is merely shown as an example and no limitation of the invention is implied.

In FIG. 2, the pumping system 70 is included in a single housing 90. Further included in the housing as part of the pumping system is a user interface 100. In this case, the user interface comprises a keypad 102 having certain keys for use in providing data and control of the pump, and a visual display 104. The display may also have touch screen capability so that it not only functions as a visual output device, but also functions as an input device. In that regard, items displayed on the display screen can operate as keys and be selected or activated by touching them on the screen. The keypad 102 may also be a part of the display 104 in that the keys may be "soft" keys displayed on the touch screen 104 which are selectable by merely touching them. In a different embodiment, the keys of the keypad may be hardware keys that are pressure sensitive, which are also well known in the art. Such devices are also well known and no further details of their construction or operation are presented here.

The touch screen display 104 of FIG. 2 shows the selectable keys of "Start", "Date", and "Time", "Volume To Be Infused", and "Delivery Rate". Activation of the "Start" key is meant to instruct the pump to begin pumping. Once started, the "Start" key is replaced by a "Stop" key in this embodiment. The selection of the "Stop" soft key would result in the pump stopping its pumping action. The "Date and Time" key when activated ("activated," "selected," "touched," and "pressed" are used interchangeably herein) permits the user to update the correct date and time in the pump's memory for use in time stamping the records established in the pump's internal log of the medication deliveries it makes. Also, having an internal clock enables advanced time-based programming of the pump so that complex fluid delivery programs may be used. The two base function parameters of "Volume To Be Infused" and "Delivery Rate" comprise the programming instructions of the base function of the pump; i.e., base function programming. Additional information such as patient identification, drug identification, as well as other data may also be displayed.

Based on the observations recited above in the Background section, the base function of an infusion pump is to controllably deliver a solution at a specified delivery rate and at a total volume to be infused. While there is a need to be able to prime or flush the medication delivery set (tubing, valves, cannula, and other items in the delivery path of the medication to the patient) so that air is purged before delivery, this is a maintenance function separate from the base function. Typically, infusion pumps have a preprogrammed "prime" feature under which the pump runs at a preselected rate to move fluid completely through the infusion set to purge air. This is a "hard" programmed feature and in some cases, changes to it cannot be made.

Other maintenance or basic input and output system ("BIOS") functions are keypad communications, video control over the display, power control, communications controls, and others. These are not meant to be included in the "base function" of the device since they are common to many processors. Instead the "base function" of the device is intended to relate to the purpose of the existence of the medical device, such as pumping medication, providing pressurized gas for respiration, pumping nutritional substances, etc.

As discussed in some detail above in the Background section, having multiple pumping channels controlled by a single central processor that is controlling each pump to deliver under an advanced delivery program that is executing in the central processor increases the probability that the software, hardware, user interface interaction, and timing requirements will be in conflict and result in an error condition. In accordance with an aspect of the invention, a medication delivery device is not controlled by a separate processor running an advanced delivery program.

A base function program is typically stored in a non-volatile memory such as a read-only-memory or flash memory or other, and has a fixed set of programmable functions, that respond in real time. This is in contrast to an "advanced delivery program" that typically has instructions going beyond a simple base function program, although it may be no more than controlling a series of base functions having different or changing parameter sets. An advanced delivery program is typically placed in a volatile memory. Such base function programs control the base function of the medical delivery device when it is started up and automatically assume operational control over that base function or functions. As an example, the base function program of an infusion pump may be placed in a ROM or EEPROM, or other type of ROM or re-writable ROM, that is non-volatile, and controls the base function of the infusion pump; i.e., delivery rate and VTBI. There may be other programs but they will generally have control over maintenance or peripheral functions of the pump and do not directly affect the delivery rate or volume to be infused. An advanced program in today's systems is typically run on a CMU which controls the pump in real time in accordance with that advanced program.

In accordance with the above aspect of the invention, there is provided a medical device, the operation of which is defined in terms of base function of the device.

Example 1: the base function of an infusion pump is "Volume To Be Infused" (VTBI) and at what "Delivery Rate." All advanced programming of an infusion pump is a function of VTBI and delivery rate with the ability to determine the timing of when to start delivery.

Example 2: the base function of a ventilator is "Volume To Be Delivered" (VTBD) and "Frequency." All advanced programming of a ventilator is a function of VTBD and frequency with the ability to determine the timing of when to start based on patient response. (Note: VTBD may be defined as absolute volume, if the ventilator is used to assist the patient, when patient breath equals or exceeds volume to be delivered, the ventilator does not cycle. In its base operation therefore, the ventilator did deliver a specified volume as a result of delivery resulting from patient activity.)

The basic premise to the above is that the delivery system can be broken down into a series of base function deliveries. The complex or advanced programs are merely a series of the base function carried out in a specified order. As used herein, the term "medicine" or "medication" is meant to be used in its broadest sense. That is, it includes any drug or remedy, including medicaments, air or other gases, food, and may include others.

Figure 3:
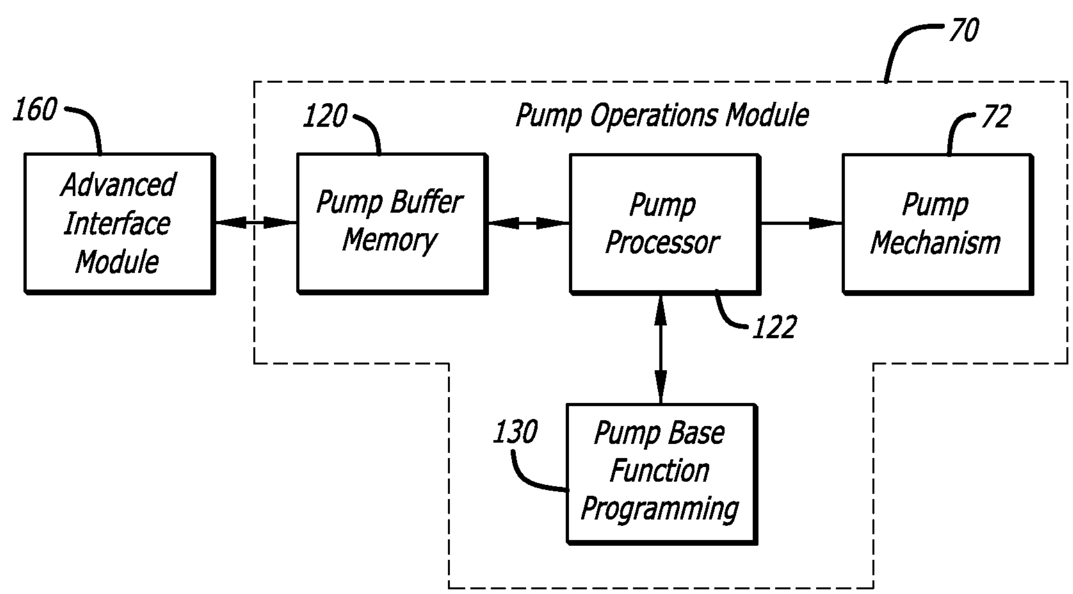
FIG. 3 is an overview block diagram of an advanced interface module connected with a pump operations module in which the two are communicating.

In accordance with an aspect of the invention, the medical delivery device has no advanced programming embedded in the medical device itself; only the programming to implement the base function of the medical device is permanent. Furthermore, the integral local controller of the medical device operates autonomously and is not configured to operate under any direct external real time control by a remote processor (such as an advanced interface module "AIM"). Referring now to FIG. 3, even if an AIM 160 is connected with the medical delivery device such as the pump operations module 70 in this case, that AIM is not able to exert any real-time operational control over the medical delivery device. The AIM may be able to collect data in real time from the medical device or check the status of a medication delivery to a patient in real time, but cannot directly control the medical device in real time. Furthermore, the front panel programming of the medical device is limited to control over the base function of that particular medical device but does not enable the user to create an advanced complex delivery program for the medical device. In the example of an infusion pump, the front panel is used only to program the delivery rate and the VTBI; it cannot be used to write a complex delivery program, such as that described below. However, in accordance with another aspect discussed below, advanced programming of the integral processor of the medical device can be indirectly effected from an outside source.

Figures 4, 5:
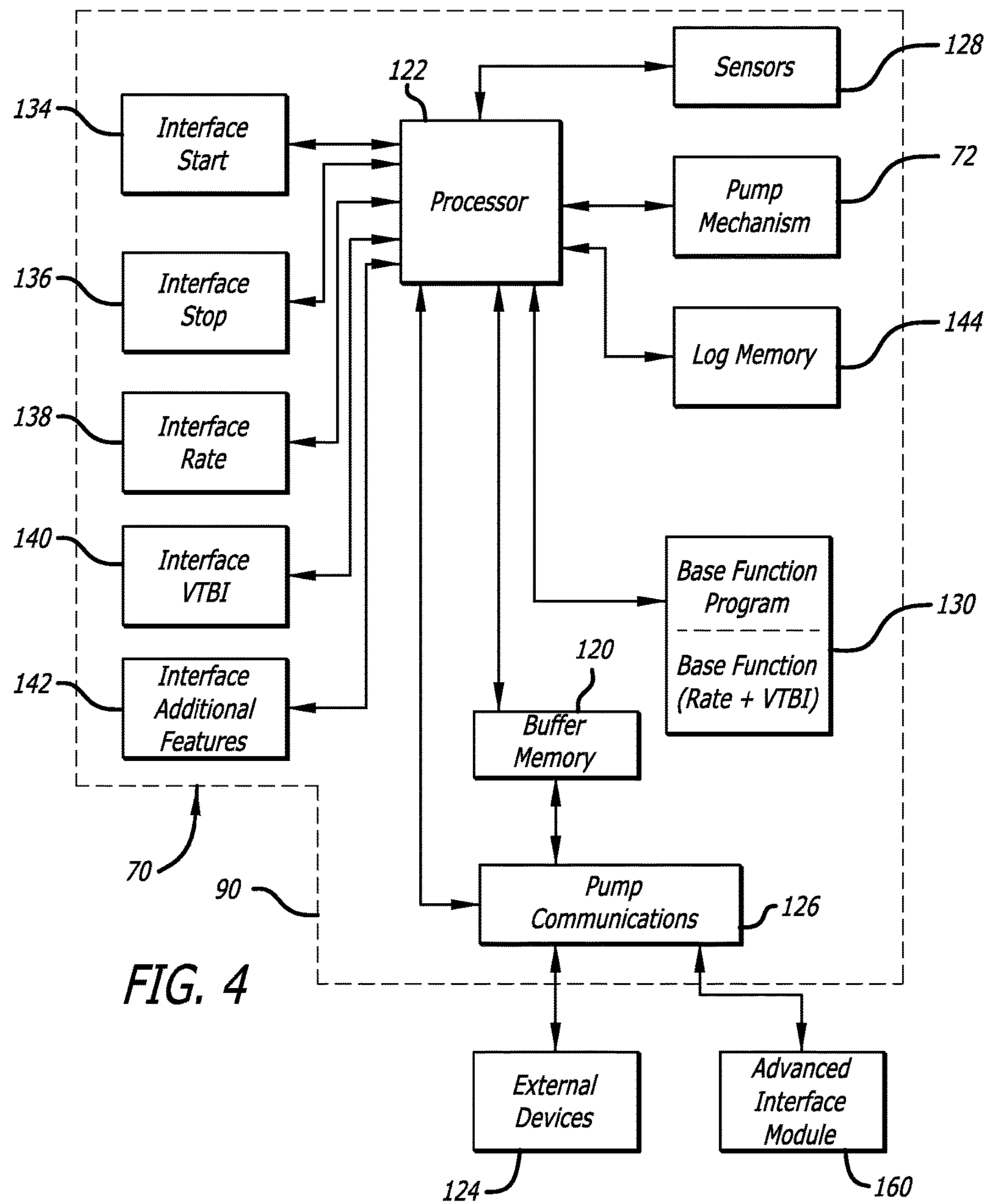
FIG. 4 is a block diagram of an intravenous (IV) infusion system in accordance with aspects of the invention in which the embedded operational program in the pump's memory is limited to controlling only the base function of the pump; i.e., rate of delivery and volume to be delivered, and showing a buffer memory into which a remote processor, such as an advanced interface module, uploads advanced delivery programs for use by the pump's integral processor to vary the delivery rate and volume to be infused in a more complex manner.
FIG. 5 is a block diagram showing an infusion pump receiving an upload of an advanced delivery program from an advanced interface module (AIM), and the AIM also being configured to monitor the performance of the pump in executing the uploaded program.

Now referring to FIGS. 2, 3, and 4, in the case of an infusion pump operations module 70, a buffer memory 120 is included that is large enough to receive and store advanced delivery programs. The integral local processor 122 is programmed to access the buffer memory periodically and if a complete advanced delivery program is found there, the local processor will execute that program autonomously. By autonomously, it is meant that the integral local processor 122 executes the program on its own without being under the real time control of, or dependence on, a remote processor such as the AIM 160. While the integral local processor 122 may also export status data to an external device 124 including the AIM 160, or a remote server or processor of another type, the integral local processor 122 will carry out the buffer memory 120 advanced delivery program without accepting further input from an external device. FIG. 3 presents an overview diagram of a system and method in accordance with aspects of the invention. An advanced interface module 160 is shown in which advance delivery programs may be created, tested, and uploaded to a medication delivery device. In this case, a medication delivery device is shown, which is a pump operations module 70. The pump operations module 70 includes a buffer memory 120 for accepting advanced medication delivery programs from the AIM 160, as well as other data and instructions, a processor 122 a pump mechanism 72, and the pump's base function programming 130.

Execution of an advanced program may be stopped by the user pressing the "STOP" key on the front interface panel 100 of the pump 70 (FIG. 2). At that time, the user may continue to operate the pump from the front panel, to deliver a bolus for example. The user may also decide to go back to the advanced delivery program by pressing a CONTINUE key (not shown). Thus, an advanced delivery program can be overridden at any time from the front panel, but can be restarted also. As discussed below in detail, the ability to create such an advanced delivery program cannot be done at the pump itself but instead, must be performed externally to the pump and the program uploaded to the infusion pump operations module buffer memory 120.

In the infusion pump operations module 70 of FIGS. 3 and 4, a local processor 122 controls the operation of a peristaltic pump mechanism 72 as to delivery rate and VTBI (base function). Sensors 128, such as pressure and air in line, are monitored by the local processor. The processor is programmed by its base function program 130 that is located, in this embodiment, in a read-only memory (ROM) 132 located in the housing 90 of the pump operations module. The base function program 130 could be an electrically erasable programmable read-only memory (EEPROM), or other non-volatile memory device, located by itself or with other memory devices in the pump system. The processor 122 also accepts commands or instructions from various interface devices. An "Interface START" key 134 instructs the processor 122 to control the pumping mechanism 72 to begin delivering fluid 74 to the patient 84 (see FIG. 2). An "Interface STOP" key 136 instructs the processor to control the pumping mechanism to stop delivery of the fluid 74 to the patient 84. The "Interface RATE" key allows the user of the pump operations module to select a delivery rate, from which the processor will determine and control the pumping mechanism to deliver controllably fluid to the patient at the programmed rate. The "Interface VTBI" key allows the user of the pumping operations module to select a volume of fluid to be delivered, from which the processor will determine and control the pumping mechanism to deliver controllably fluid to the patient until the programmed volume has been reached. The interface includes additional features 142 not discussed here in any detail, but which may include confirmation of a patient's name or other identification, user's name or other identification, etc. The pump operations module 70 also includes a log memory 144 in which the processor 122 stores pump events, such as programmed rate, VTBI, time of start, time of stop, sensor readings, and other data. All of the above are enclosed in a single housing 90 in this embodiment as shown.

FIG. 5 presents a block diagram of a medical device (in this case an infusion pump operations module 70 described above) connected with an Advanced Interface Module ("AIM") 160. The AIM and the pumping operations module may be interconnected 164 in this embodiment with a hardwired connection, optical, wireless, RF, or other or combination of these. The AIM, in this case, has a built in monitor 166 that can be used to monitor progress of fluid delivery by the pump, sensor readings, or other data generated by the pump system. It is shown as being connected by a separate data conductor 168, but this can also take other forms, such as a wireless communication system as described above. Additionally, it may be a part of the connection 164 of the AIM 160 with the pump operations module 70. It can also be used to view, but not change, the delivery rate and VTBI of the pump operations module 70. The monitor 166 is also usable to view the creation of an advanced delivery program for upload to the pump operations module 70. In that regard, the monitor may have at least two modes; internal and external. It can also be used to monitor the upload of an advanced delivery program to the pump operations module. As will be discussed below, if a single AIM is in connection with multiple medical delivery devices simultaneously, the monitor 166 can switch between each for monitoring purposes or can present a "tile" view on a single screen of the data from multiple devices. Other presentations of data are possible.

An AIM 160 can comprise various computing devices. If its purpose is to do no more than prepare advanced delivery programs for infusion pump operations modules for example, many computers would function well. If the AIM is needed to monitor the progress of the treatment provided by a medical device or plural medical devices, then the AIM may need certain display configurations and software for processing, displaying, and recording data signals. Many touch screen computers should function efficiently in providing the advanced programming and monitoring screens for several infusion pumps. Monitoring screens should provide the appearance and functional requirements of the "specific patient population," for example, neonatal, anesthesia, critical care, pediatric, emergency, and others.

Figure 6:
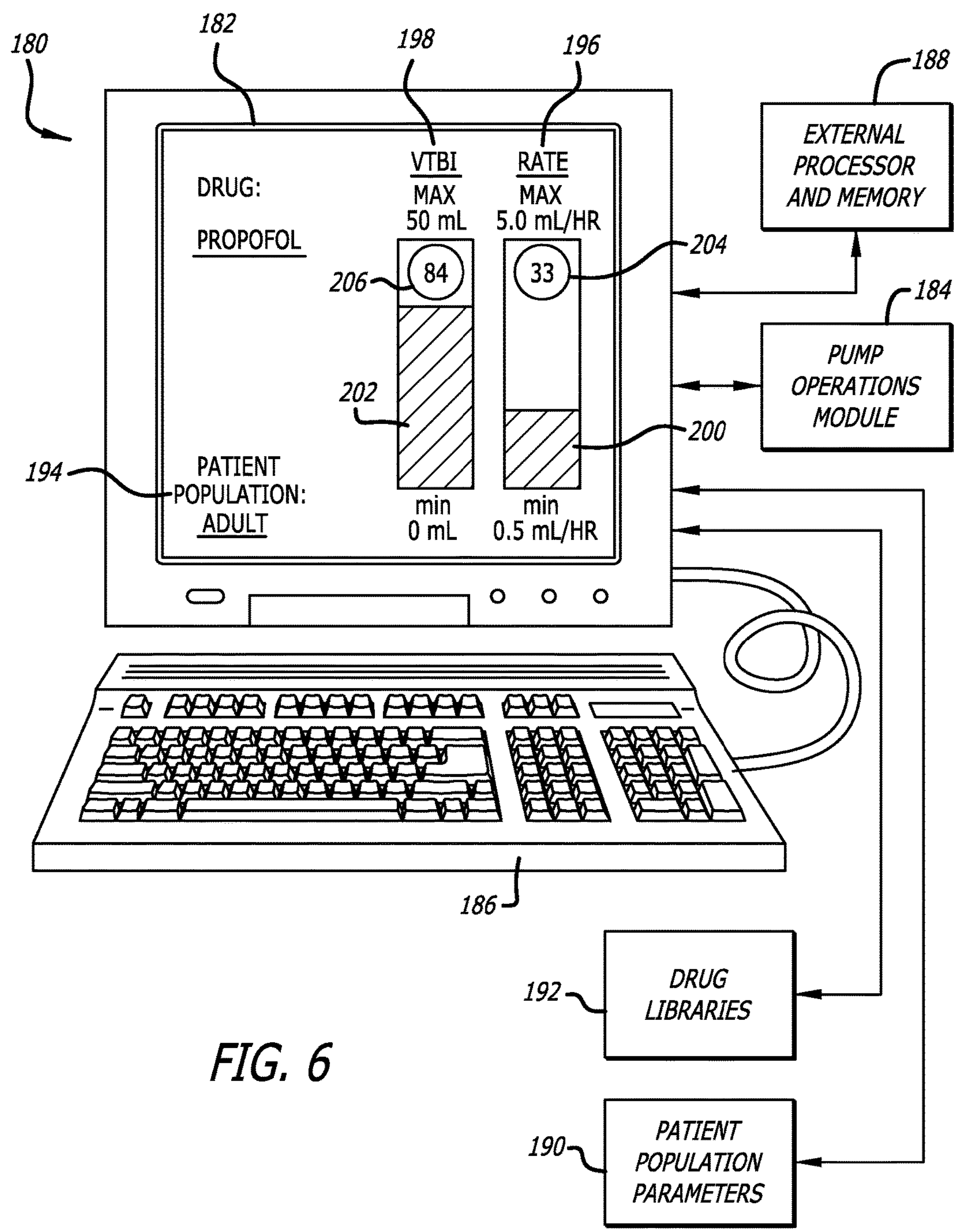
FIG. 6 shows an advanced interface module (AIM) having a graphical input for entering control data or other data, this graphical input being in the form of touch screen slider controls in which a range is provided with a cursor located within the range and moveable between one end of the range and another end of the range, the touch screen feature in this embodiment allowing for direct movement of the displayed cursor between maximum and minimum limits placed on the screen at respective ends of the range by access to drug libraries and patient population parameters, all selectable at the AIM, also showing the AIM connected with an infusion pump and an external processor, that may be with a healthcare institution, pharmacy, medical records storage service, or other.

In an aspect of the invention, a graphical input device is provided. In one embodiment, a touch screen is used to display slide controls for setting desired rates and VTBIs. A range is shown within which a cursor may be moved to select a "value" or "level." The graphical slide controls are presented with the actual limits appropriate for the respective patient population in this embodiment. Neonate critical care verses adult fluid replenishment is an example in which the limits may be quite different and the selection of the wrong key from a keypad could result in incorrect drug delivery. Referring now to FIG. 6, there is presented a limited example of the use of a graphical input device. An advanced interface module (AIM) 180 includes a touch screen 182 with which a user can create an advanced delivery program for upload to a medical infusion pump operations module or can monitor the performance of an infusion pump, or both. In this case, the AIM has a second input device of a keyboard 186. An external processor 188 may be connected with the AIM. Either the external processor or an internal AIM memory may include patient population parameters 190 and drug libraries 192. See U.S. Pat. No. 5,681,285 to Alan D. Ford and Nathaniel M. Sims and Marc A. Mandro, incorporated herein by reference, for more detail on drug libraries. The external processor may operate as only a memory in which data from the AIM 180 or its connected pumps or patient monitors are communicated to be stored, analyzed, or other, or from which program and control instructions can be received.

In the case where drug libraries 192 are available to the AIM 180 and they include predetermined limits on the drugs in the libraries for various patient populations, then selection of a particular patient population 194 key on the touch screen 182 will enable the display of the drugs for that population as well as the limits for each drug specifically designed for that population. For example, in FIG. 6, the drug "Propofol" has been selected. The maximum and minimum delivery rate and VTBI are shown as graphical slide controls 196 and 198 respectively. In this case, the slide controls have a vertical orientation but in another embodiment, they may have a horizontal orientation, or other. At the top of the slide controls are the maximum values for the drug and at the bottoms are the minimum values.

In this embodiment, the touch screen 182 is used to display the slide controls and by simply using a finger to move the cursor or "slide" 200 and 202 of each control, the values can be set. Because a keypad is not used, and the maximum cannot be exceeded for that patient population with this graphical slide control approach, it will be much more difficult to make medication programming errors. The drug library will automatically set the maximums and minimums for the particular medication and the user is unable to change them. Additionally, using a graphical slide control shows the user a "relative" setting between maximum and minimum. In many cases, a physician or nurse knows that this patient is supposed to receive approximately an "average" dose of the drug, and seeing that the slide falls about in the middle will reinforce that the setting is correct in the mind of the user. If on the other hand, the physician or nurse believes that the patient is to receive an average dose, but the slide is near the maximum value, a possible error will be made apparent. Thus common errors with striking the wrong key on a keypad are obviated.

In another feature shown on FIG. 6, the slide controls present a percentage value 204 and 206 somewhere near, on, or above the slide 200 and 202. In the case of delivery rate in FIG. 6, the percentage is thirty-three and in the case of VTBI, the percentage is eighty-four. In another embodiment, an absolute number may be shown for the slide setting rather than, or in addition to, a percentage.

The same graphical slide control approach can be used with an infusion pump operations module 70 that has a touch screen, with the same benefits being realized. The use of such slide controls and drug libraries within a healthcare facility can prevent significant over/under infusions as a result of programming errors.

In another aspect where a plurality of infusion pump operations modules are needed, touch screens can provide real-time pump operation status. In the event of a pump operations module or pump operations modules experiencing an alarm condition, the AIM screen can provide a clear indication of which pump operations modules are in an alert condition. Separation of advanced programming module from the pump operations module and use of touch screen programming at the AIM to enable the use of advanced delivery programs ensures that programming controls do not negatively affect a specific pump operations module and potentially lead to multiple pump operations modules going into alarm conditions. Tying the patient identification ("ID") and the drug ID to the pump, and graphical programming with touch screens support better drug delivery controls and appropriate security to ensure proper linkage between the pump operations modules and the advanced programming module.

The size of the screen should be selected to support user needs during the programming and continuous monitoring of the pump operation. If the AIM display is to be used to monitor a plurality of infusion pumps at once, and a "tile" type of display is to be used in which a plurality of tiles, one for each pump, is to be displayed simultaneously so that all pumps can be monitored at once, the screen size of the AIM should be large enough to accommodate the entire plurality of tiles so that they can be seen clearly from a predetermined distance, perhaps three meters.

Much can be gained from the knowledge used in the development of video games. A video game console is typically an interactive entertainment computer or modified computer system that produces a video display signal that can be used with a display device, such as a high-definition monitor or a television, to display a video game. Typically, high quality audio is included that is played through the speakers of an audio system or the television. The term "video game console" is used to indicate a machine designed for consumers to buy and use solely for playing video games as opposed to a personal computer which has many other functions. A console video game is typically an interactive multimedia game used for entertainment. The game consists of manipulatable images and audio, sometimes very high quality and generating a three-dimensional type image, generated by a video game console, and displayed on a television or similar audio-video system. The game itself is usually controlled and manipulated using a handheld device connected to the console called a controller, that generally contains a number of buttons and directional controls each of which has been assigned a purpose for interacting with and controlling the images on the screen. The high quality and rapidly changing images, audio synchronization, and a controller providing constant inputs can cause enormous amounts of data to be generated, that must be processed to avoid freezing images, crashes of the console, and other disabling effects. Many approaches used in such an environment to keep everything running smoothly can be adapted to the medical field as well.

Video console games require a much more advanced control of software design and operation than games designed to play on computers. The console has very specific limitations of controller speed and memory. Therefore, the designers must recognize the limitations of the software/hardware interface. At the same time the designers must recognize that the user interaction is expected to be as responsive as the computer game. If the users' experiences are different, then the console game is not acceptable to be released to the market. The traditional pump design functions similarly to a game console with the program installed. The comparison to the game console is to show the effect of processor speed and memory size impact on how complicated the game can be. The system and method in accordance with the invention has moved a pump from a game console to the comparison with a printer, by removing the advanced programming capabilities from the pump and adding a large buffer. The pump operates more like a printer receiving a request to print multiple documents in a specific order. Both comparisons are provided to more clearly see the benefits. Embedded advanced programming with super users results in unexpected anomalies and drug delivery issues. Providing a separate advanced interface module dedicates the pump operations module processor and memory to only controlling the base drug delivery function. The complex algorithm user interface (AIM) is isolated from the pump processor with the exception of the most basic programming. The paradigm shift is the move from the game console model to a printer model.

In accordance with an aspect of the invention, the user can select values for parameters of the base function of the medical delivery device without using an advanced interface module (AIM). For example, in the case of an infusion pump operations module, the user can set a delivery rate and a VTBI from the front panel of the pump operations module itself. In most cases this addresses the vast majority of the most common uses of the medical device. All medical device system operations, monitoring, and error notices are controlled by the device itself independent of an AIM. However, the medical device has buffer memory 120 (FIGS. 3 and 4) to accept and store user instructions sent to it from the AIM 160 (FIGS. 3 and 4). The medical device also has a history log 144 (FIG. 4) to maintain a record of activity and error conditions. Medical devices designed to support only their base function will never require software updates to support new protocols or updated drug libraries. Base medical device operation is the same for all users while such updates to protocols and drug libraries can be handled by the AIM alone.

The advanced interface module (AIM) has any number of advanced programming tools included in its user interface options. The AIM allows the user to program any number of base function instructions that, when executed as specified, deliver the desired therapeutic outcome. For example, delay the start for 10 minutes, then deliver a bolus of 20 ml in 2 minutes (VTBI=20 ml, rate=600 ml/hr),
then deliver 30 ml at 5 ml/hr,
then deliver bolus of 20 ml in 2 minutes (VTBI=20 ml, rate=600 ml/hr),
then deliver 30 ml at 5 ml/hr,
then deliver a bolus of 20 ml in 2 minutes (VTBI=20 ml, rate=600 ml/hr),
then deliver 30 ml at 5 ml/hr,
then deliver a bolus of 20 ml in 2 minutes (VTBI=20 ml, rate=600 ml/hr), and
then deliver 80 ml at 5 ml/hr, for a total delivery of 250 ml.

It must be understood that all advanced programming features require the use of rate and volume to be infused, which are base functions. The advanced features then add delay starts, series of rate/volume to be infused commands, and predetermined calculations that allow rate and total volume to be infused (VTBI) to be determined by specific patient data and therapeutic outcomes.

In accordance with further aspects, an advanced interface module (AIM) provides a graphical representation of the proposed therapeutic delivery schedule and the actual therapeutic delivery within ±24 hours. An AIM provides visually enhanced status of each device programmed using the AIM. An AIM may be connected to the medical device in the following manner, direct wire, Wi-Fi, Bluetooth, optical, or RF. An AIM may be connected to multiple medical devices, and is not limited to a single type of device. Examples are infusion pump operations modules, an $SPO_2$ monitor, an EKG monitor, and a ventilator. An AIM has the ability to collect data from various monitoring devices and update scheduled delivery based on patient response. Protocols where defined patient response dictates an increase or a decrease in delivery are examples of this capability; always per instruction of a physician or under specific hospital protocol. For example, 40% oxygen at 5 l/min until patient $SPO_2 \geq 95\%$ for 2 hrs., reduce to 40% oxygen at 1 l/min, but if $SPO_2$ drops $\leq 92\%$, return to 5 l/min.

An advanced interface module (AIM) may be supplemented with predictive models to allow the user to optimize the therapeutic plan for the patient, although medical practitioner interaction and verification is always required. An AIM has touch screen capabilities and may allow a mouse or a keyboard interface when appropriate or desired. An AIM's records are stored in files specific to individual patients and can include the drugs delivered, what each medical device was instructed to do, device data logs from start of therapy to removal from use on the patient, patient identification, and additional information added by medical personnel into a patient record. Further, an AIM's features may support formatting the stored data into patient records and sending them to the healthcare facility's patient records data archive, or elsewhere, such as an online Internet medical records storage service (Google™ Health). An AIM also has the capability of automatically downloading scheduled information into a facility's IT system as desired.

The advanced interface module can also take the form of a personal computer such as a laptop or tablet computer, or a personal data assistant, or other device with which infusion pump programming can be created. In the preferred embodiment, the advanced interface module 160 has a separate housing from the infusion pump operations module 70 (see FIG. 4).

It will be noted that there are significant paradigm shifts in the above. In particular, advanced delivery programming features are not embedded in the infusion pump operations module. Separate touch screen computers are used to control and support the advanced programming features required to provide healthcare-approved protocols in one embodiment. The touch screen is developed to enable a user to intuitively program the advanced programming options that are made available. In another embodiment, the communications could be wireless with a central touch screen at a nurse's station (or elsewhere) that permits a clinician to call up a patient. The delivery parameters would be in place and they could be altered from a central panel, sending instructions to each pump at the bedside (similar to a wireless shared printer). If wireless communications could be safe enough, one could eliminate having a touch screen connected to every device, and rather use a central touch screen that would wirelessly send commands to the devices.

A programming touch screen located on an advanced interface module (AIM) in accordance with one aspect of the invention supports four to six infusion pumps assigned to a specific patient. The programming screens of the AIM are designed for specific patient populations and therapies, for example:

a. Anesthesia;
b. Critical Care;
c. Emergency;
d. Gene therapy.
e. General Care;
f. Neonatal Critical Care; and
g. Pediatric.

The programming touch screen of the AIM supports specific patient population drug libraries, it supports patient identification ("ID") and drug ID, it supports specific patient therapy, it is capable of communicating (one way initially) wirelessly with central data control system(s), or other remote processors and data storage and processing facilities. It supports advanced programming features by communicating to specific patient-assigned pumps each delivering a specific drug. The software of the AIM and the programming touch screen may be upgraded when not in use with a medical device. Touch screen capabilities include graphical slide control features for setting volumes and rates and the touch screen supports patient monitoring status on the screen if desired by a practitioner.

To briefly reiterate, the base function of an infusion pump operations module in accordance with aspects of the invention is to deliver a medical fluid at a desired rate and total volume to the infused. The infusion pump operations module also provides a means to prime or flush the system, the display screen is simple and provides rate, volume to be infused, and total volume infused, the patient identification (ID) can be entered or scanned, the drug identification (ID) can be entered or scanned, and a wired or wireless interface is provided between the infusion pump operations module and an advanced interface (programming) module (AIM) having a touch screen. In an aspect in accordance with security aspects of the invention, the patient ID is linked between the pump and the AIM through the AIM programming touch screen to ensure that the pump operations module is programmed by only one programming touch screen at any given time. This is part of the system security to limit the wireless communication of a programming touch screen to a single patient.

There is a need to deliver very small volumes to support developing therapies and change the paradigm of drug use in the hospital. Currently drugs are controlled and distributed at multiple dilutions. This is a critical control point for the proper delivery of drugs to all patients. The multiple dilution options are required to support the drug use to multiple patient populations. Heparin errors result when a higher-than-ordered concentration is delivered to the neonate department. The lower concentration is required because the infusion pumps currently on the market cannot deliver a single concentration of heparin to all patient populations. Gene therapy is a developing therapy that requires the use of micro-liter (μl) units of measure. There are infusion pumps approved for laboratory use but none for human therapy use. Other than the size of syringes used and therefore the range of delivery rates and volumes, the requirements are the same. Disposable requirements need to be developed to support the lower delivery rates and volumes. The invention is applicable to syringe delivery, large volume pump (LVP) delivery and others, and is not specific to any particular form of delivery, but rather addresses the buffer issues needed to have clear instruction execution.

By limiting the pump operations module to its base function of providing rate and total volume delivery with a system prime or flush option and moving all advanced programming features to the touch screen of an advanced interface module (AIM), the master/slave model currently used in the intravenous pump industry is eliminated. The new model is more appropriately defined as a general/soldier relationship. The individual pump (soldier) has control of its operation and performance and has its own power source. The AIM programming touch screen (general) has determined a strategy that is communicated to the pump when the pump has completed the current task. The AIM also has its own power source. A soldier is told to take the hill and report back when the hill has been secured. The general will then provide the next instruction to achieve the desired strategy. Similarly the AIM programming touch screen communicates the first required rate and total volume to be delivered to the buffer memory of the pump operations module. Once the delivery is completed by the pump operations module, the AIM programming touch screen communicates the next required rate and total volume to be delivered.

Each pump operations module is a stand-alone device that is capable of accepting a single rate of delivery and total volume to be infused. The AIM has been loaded with capabilities that meet all the envisioned needs of the specific area of the hospital. The AIM interface is conducted separate from the pumps when the AIM is used, and therefore, there is no risk of timing conflicts between the AIM and the pump operations module. The AIM is configured with effective human factor interfaces that support intuitive programming and eliminate keypads for numeric data entry.

Although FIG. 5 shows only one infusion pump operations module 70 connected to an advanced interface module (AIM) 160, it is possible to have a plurality of pump operations modules connected to the AIM. It is one of the advantages of the invention that the AIM can simultaneously be connected with a plurality of pump operations modules and other devices and can monitor all of them. The display screen of the AIM may need to be switched between each of the infusion operations modules for monitoring, or in another embodiment, the AIM's display screen may be split into four quarters or other arrangements of multiple sub-screens in which each quarter displays the monitoring data from a different pump system. By being connected to a plurality of pump operations modules, an advanced programming infusion routine prepared on the AIM can be uploaded to each pump operations module simultaneously. This could have application where the delivery of drug interactions are established and established protocols have been loaded into the AIM, or to support nurse station updates when new patient orders are received via the electronic patient record or other hospital communication tools.

Figure 7:
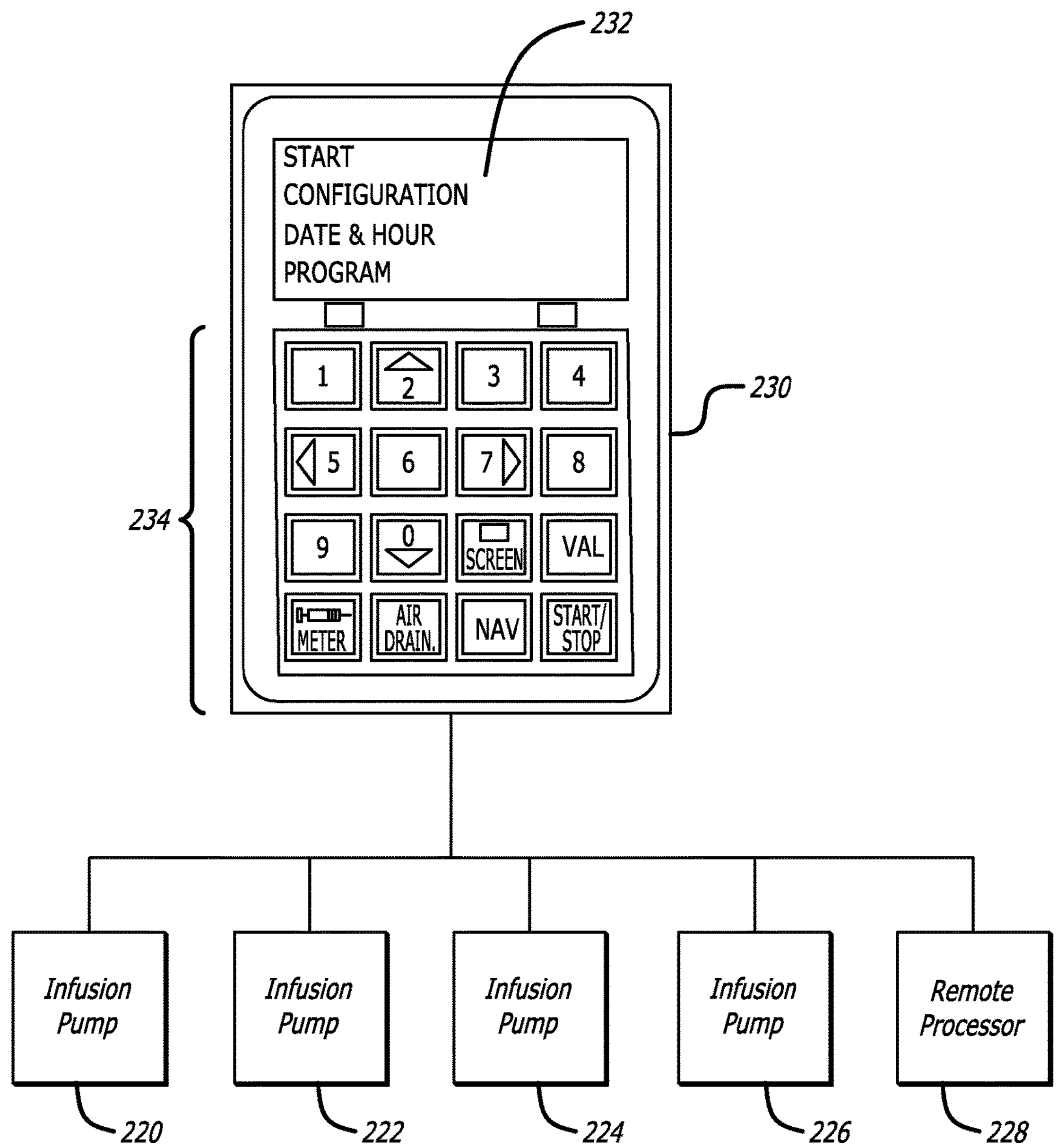
FIG. 7 is a block diagram of a single AIM connected with four separate infusion pumps, that may all be connected to the same patient, for uploading advanced delivery programs to each pump as needed, and for providing a monitoring interface for all of the pumps at a single location, that may be selectable between each pump in one embodiment, and showing connection to an external server that may include a healthcare institution's pharmacy server or other.

Referring to FIG. 7, an embodiment of a system of a plurality of infusion pump operations modules 220, 222, 224, and 226 connected with an advanced interface module 230 is shown. The infusion pump operations modules may be the same as that shown in FIG. 3 or 4 or may have different forms. Also, instead of all being infusion pump operations modules, one or more may be a different medical delivery device, such as an oximeter, ventilator, respirator, dialysis machine, enteric device, or other. The AIM includes a graphical input device, such as a touch screen 232, and a second input device 234 which in this case comprises a keypad with which the individual digits of a level or value may be manually entered sequentially. The invention is shown in which a dedicated advanced interface module 230 (AIM) is shown that is connected with four pump systems 220, 222, 224, and 226. Although four pump operations modules are shown, an AIM may be able to connect with many more at the same time, depending on the embodiment. The AIM may also be connected with a remote processor such as a healthcare institution's pharmacy server, or other. In another embodiment, the AIM may be located in the same housing as the pump operations module. The AIM would be configured to provide advanced programming to the delivery device within the same housing. In yet a further embodiment, the co-located AIM may also be configured to output programming to other medical devices if put into communication with them, such as by wired or wireless communication. They may be outside the housing and may be remote depending on the situation.

Pharmacokinetic System

As noted above, the advanced interface module (AIM) is configured to program selectively and monitor a plurality of drug delivery systems to deliver drugs in different modes. The delivery of drugs at a predefined rate and volume, and delivery of a bolus dose are generally conventional. However, the AIM is also able to deliver drugs through a plurality of drug channels (infusion pumps) in accordance with a pharmacokinetic (PK) model. The PK model can be resident in an AIM and can be used to program the rate of drug delivery to achieve either a desired blood plasma drug concentration of the drug within a patient's body, or a desired effect compartment drug concentration for the drug.

Briefly and in general terms, "pharmacokinetics" includes the study of the mechanisms of absorption and distribution of an administered drug, the rate at which a drug action begins and the duration of the effect, the chemical changes of the substance in the body, (for example by enzymes), and the effects and routes of excretion of the metabolites of the drug. Pharmacokinetics describes how the body affects a specific drug after administration. Pharmacokinetic properties of drugs may be affected by elements such as the site of administration and the dose of administered drug. These may affect the absorption rate. Compartmental PK analysis uses kinetic models to describe and predict the concentration-time curve.

Figure 8:
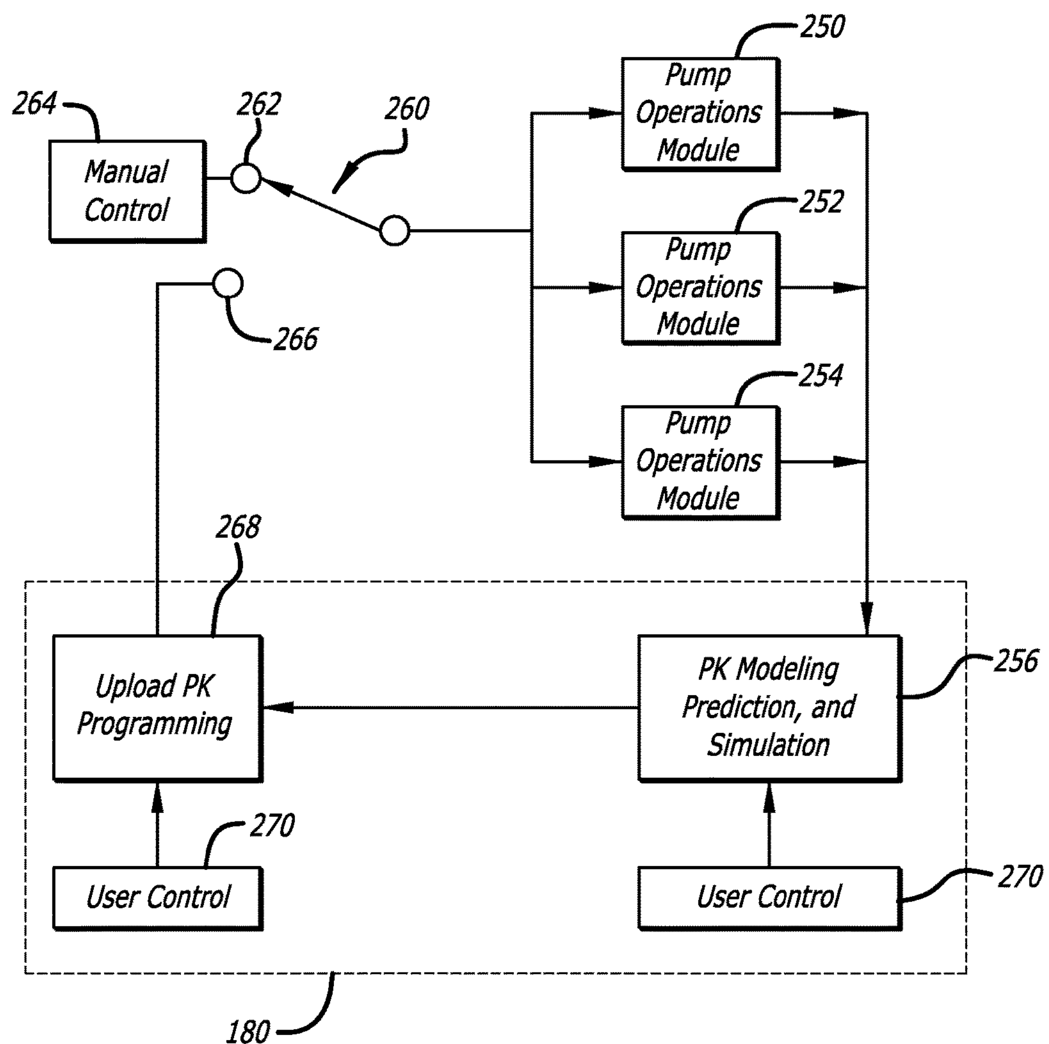
FIG. 8 is a block diagram of a pharmacokinetic system incorporating aspects of the invention in which three infusion pumps are used on the same patient, along with a switch device to switch control over each of the pumps to a manual mode or to an advanced delivery program, and a PK modeling and prediction portion that monitors the operation of each of the pumps to predict the necessary PK levels, all under user controls.

A functional block diagram of a PK model 256 used by an AIM 180 in programming a plurality of pumps is shown in FIG. 8. As is described in more detail below, the plurality of infusion pump operations modules 250, 252, and 254 are programmed according to the role each one is to have in carrying out the PK model. Since none of the pump operations modules have embedded advanced programming, the user has the option of selecting either to control drug delivery at each pump operations module in accordance with a PK model advanced delivery program uploaded to each pump operations module, or alternatively, to administer a drug through manual control of the pump operations module, either as a bolus dose or as a continuous infusion at a selected rate. It is important to note that control of the drug delivery rate in accordance with the PK model can be interrupted at any time, should the user switch to manual control of the pump operations module to deliver a bolus dose or to provide a selected rate of continuous drug infusion. Delivery under the control of the PK model can then be selectively resumed.

This user-selective option for controlling the infusion of drugs is represented by a switch 260 in FIG. 7. In a first position 262, the switch selects the infusion of drugs in accordance with manual control 264 over the pump operations module, and in a second position 266, the switch selects the infusion of drugs in accordance with the uploaded advanced delivery program 268 consistent with the PK model 256.

Assuming that switch 260 has been selectively set by the user to administer drugs in accordance with the PK model 256, the AIM 180 uploads 268 an advanced PK delivery program to one or more of the infusion pump operations modules 250, 252, and/or 254. Those programmed pump operations modules upon executing the advanced PK delivery program, set the rate of drug delivery to achieve either the desired blood plasma drug concentration selected by the user, or the desired effect compartment drug concentration.

The source of these control signals is represented in FIG. 7 by the PK Model block 256. As further shown in FIG. 7, a user 270 may provide the user input to the PK model and prediction block 256 corresponding to a selected set point. Furthermore, the AIM monitors each of the infusion pump operations modules 250, 252, and 254 so that delivery data can be considered in the modeling and prediction.

The AIM 180 executes the PK simulation in block 256 to determine current model data and the predicted drug concentration (blood plasma and/or effect compartment) that are periodically supplied to the Upload PK Programming block 268. Either type of drug concentration set point can be changed 270 at any time and the PK model will provide a revised advanced PK delivery program for the administration of the drug to achieve the new set point. An update timer (not shown) establishes the time interval at which the current model data and predicted drug concentration are transferred from the PK modeling, prediction and simulating in block 256 to the Upload PK Programming in block 268.

In accordance with a PK model controlled delivery, a desired set point is achieved by controlling the multi-channel drug delivery system to attain the desired set point based upon a predicted drug concentration within the patient produced by compliance with the model. The predicted concentration of each drug administered by the multi-channel drug delivery system is continuously modeled throughout an entire patient case, regardless of: (a) the control mode that is selected, (b) any interruption of the drug delivery that may have occurred, or (c) termination of the drug delivery. The PK model control delivery can thus be initiated at any time, interrupted, and then resumed. A first drug can be administered through one drug channel 250 under the PK model 256 by use of the manual mode 264 of a pump, a different second drug can then be administered through that drug channel 250 also by use of the manual mode 264, and the administration of the first drug can be resumed through the same or a different drug channel through use of an advanced PK delivery program uploaded 268 to the first pump operations module 250. Accordingly, even through only three drug channels are provided in the multi-channel drug delivery system disclosed above, the AIM 180 can continue to track the predicted drug concentrations of substantially more than three drugs administered to the patient, and can create revised programs for uploading 268 or indicate control over the delivery of any of the drugs using the PK model control by manual mode 264 at any time. Thus, a plurality of different drugs can be administered to a patient through any one or more of the drug channels, and PK control of the administration of any of those drugs can be selectively assumed by the controller at any time during the patient case.

The PK simulation in block 256 models the blood plasma drug concentration and/or effect compartment drug concentration of the drug being administered based upon variables that depend upon the specific drug being infused, and patient specific data such as the weight, the age, and gender of the patient. Another important variable is the actual rate at which the multi-channel drug delivery system is infusing the drug. The rate of delivery of the drug is provided to the AIM 180 as a result of monitoring each infusion pump or channel. These feedback signals, which indicate the actual delivery rate of the drug, allows the PK model to compensate for an imperfect pump response to a requested change in the rate of drug delivery, and to compensate for alarm-caused delays, and other interruptions in the delivery of the drug to a patient. The actual delivery rate also enables a more accurate drug concentration prediction to be achieved, since a pump operations module may not deliver a drug at the rate it was commanded to by the advanced PK model programming 268. Furthermore, when the user selectively operates a pump operations module under manual control, the PK simulation 256 uses the drug rate delivery information to continue to track and predict the drug concentration (either or both blood plasma and effect compartment), even though it is not controlling that rate. This feature enables the predicted rate and historical rate to be displayed to the user for each drug administered, at any time, including during manual control of drug delivery and after the delivery of a drug is interrupted or even terminated.

Although the switch 260, first position 262, second position 266, manual control 264, and Upload PK Programming 268 are shown as single items, they may include separate items for each individual pump operations module. As an example, the switch 260 may actually represent three switches, one for each pump operations module, and the same is true for other items, such as the first position 262 and the second position 266.

The specific drug that is to be administered by one of the drug channels 250, 252, or 254 could be identified with an entry by the user on a keypad or on the touch screen 182 of the user interface (FIG. 5). However, to simplify identification of the drugs to be infused, a bar code reader (not shown) can be used to scan a drug identification bar code that is affixed to each of the drug vials. Bar code readers are well known and may comprise a fixed scanner that is positioned adjacent each drug vial, or alternatively, may comprise a hand-held wand that includes an optical scanner that is moved to the drug vial to read the bar code. The AIM 180 may store or have access to drug libraries 192 listing specific drugs commonly delivered to a patient by the multi-channel drug delivery system and their PK model data, so that once the bar code on a drug vial has been scanned, the AIM 180 can determine whether the drug has been recognized as one of those for which data are stored. If PK control data are not stored for a drug, that drug cannot be administered under the PK model control in the preferred embodiment; however, it is contemplated that the required data might then be entered by the user on the touch screen 182 or a key pad 186.

The pump operating system of the pump operations module is programmed to monitor the pump operations and to deliver basic rate/delivery time/total dose programming. The pump operations module will alarm in the situation where pump operation is not functioning properly. If the communications between the pump processor and its buffer is lost this would also be an alarm situation, and the pump would stop pumping medication so as to avoid harm to the patient. However, the pump will have completed the delivery of the current delivery parameters accessed from the buffer prior to attempting to retrieve the next scheduled delivery parameter from the buffer. As mentioned above, the AIM is used to program more advanced pump instructions. Delayed delivery starts, bolus deliveries, and various algorithms used in many drug delivery protocols including TCI, as well as other advanced delivery patterns or techniques to make medications more effective for patients. The AIM contains the drug library, programming error checks, and other enhanced features. The drug library, advanced programming options and error checks are all in the AIM. The approved programming is then sent to the pump operations module as a batch of operations, each being defined as a simple rate/time/total dose step.

The user interface on the pump operations module supports only these base functions of the pump; i.e., rate and VTBI. This pump operations module user interface is a default if the advance programming uploaded to the pump operations module buffer is off line or not operating. However, the pump must be stopped to enter the base programming parameters. The pump operations module stores in a buffer the scheduled drug delivery parameters uploaded from the AIM. As each step of the uploaded buffer-stored delivery program is completed, the pump processor accesses the buffer and the next delivery instruction is started. Therefore, the pump operation never is in competition with the user interface.

It will be seen from the above, that the advanced delivery program is executed only by the operations module and is not executed by the advanced interface module with the pump being controlled thereby. Thus, should the advanced interface module crash or be rendered unusable during the execution of an advanced medication delivery program by a pump operations unit, that crash will have no effect whatsoever on delivery of the medication to a patient under that advanced delivery program. Therefore, this failure mode, which comprises a major problem with existing systems, has been removed from systems and methods in accordance with the invention.

In the above detailed description, well-known devices, methods, procedures, and individual components have not been described in detail so as not to obscure aspects of the present invention. Those skilled in the art will understand those devices, methods, procedures, and individual components without further details being provided here. Moreover, while the embodiments disclosed above are described for use in a healthcare facility environment, it will be understood that the system and method may be useful in other environments as well, such as outpatient clinics and other environments where care is delivered to a patient.

Further features and/or variations of the invention may be provided in addition to those set forth herein. For example, the present invention may be directed to various combinations and subcombinations of the disclosed features and/or combinations and subcombinations of several further features disclosed below in the detailed description.

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims.

We claim:

1. A method for the delivery of medication, the method comprising:

programming an operations processor of a medication delivery operations module, wherein the medication delivery operations module includes a delivery mechanism having a base function of medication delivery at a selectable rate and a selectable volume, wherein the step of programming the operations processor comprises programming the operations processor to set the delivery rate and the delivery volume of the base function of the delivery mechanism at fixed values;

receiving an advanced medication delivery program from a source outside the medical delivery operations module and storing the advanced medication delivery program in a buffer memory, wherein the advanced medication delivery program has a plurality of different values that vary with time for at least one of the delivery rate and the delivery volume;

programming the operations processor to access the buffer memory for the existence of a complete advanced medication delivery program, and if a complete advanced medication delivery program is found, to execute the advanced delivery program under which the operations processor automatically varies at least one of the rate of delivery and volume of delivery values in accordance with the advanced delivery program autonomously without being under real time control of, or dependent on, any remote processor or data source, including a processor at a source from which the advanced delivery program came, or a user interface, except for starting and stopping the operations processor in executing the advanced delivery program, but neither the user interface nor any other control or data device can be used to change the advanced program being executed.

2. The medication delivery method of claim 1 wherein the step of programming the operations processor further comprises programming the operations processor to override execution of the advanced medication delivery program upon receiving a STOP signal from a user interface of the operations module.

3. The medication delivery method of claim 1 further comprising:

creating the advanced medication delivery program in an advanced program processor that is part of an advanced interface module ("AIM"), the advanced program processor being separate from the operations processor;

wherein creating the advanced delivery program comprises assembling a sequence of varying base function operations.

4. The medication delivery method of claim 3 wherein the step of creating the advanced delivery program by the advanced program processor further comprises programming the advanced program processor to display a graphical image of a range of acceptable values for a selected medication from which an operator may select a value and to incorporate the selected value into the advanced delivery program.

5. The medication delivery method of claim 4 wherein the step of creating the advanced delivery program by the advanced program processor further comprises programming the advanced processor to access a memory and retrieve the displayed range of acceptable values from a library of acceptable values for a particular medication.

6. The medication delivery method of claim 4 wherein the step of creating the advanced delivery program by the advanced program processor further comprises programming the advance processor to display a cursor within the displayed range of acceptable values, the cursor being movable to a selected position within the acceptable range by the touch of a user.

7. The medication delivery method of claim 1 wherein the step of programming the operations processor further comprises programming the operations processor to control system operations of the delivery operations module, to monitor those operations, and to display error notices on a user interface.

8. The medication delivery method of claim 3 wherein the step of creating the advanced delivery program by the advanced program processor further comprises programming the advanced program processor to communicate advanced medication delivery programs to a plurality of delivery operations modules with which it is simultaneously connected.

9. The medication delivery method of claim 4 wherein the step of creating the advanced delivery program by the advanced program processor to display the acceptable range of values further comprises programming the advanced program processor to display absolute numbers at each end of the range plus a percentage value for a selected particular value within the range.

10. The medication delivery method of claim 4 wherein the advanced program processor is further programmed to display drugs for a patient population as well as limits for each drug specifically designed for the selected patient population.

11. The medication delivery method of claim 1 wherein the delivery operations module is not enabled through programming or otherwise create an advanced medication delivery program.

12. The medication delivery method of claim 11 wherein the step of programming the operations processor disables the operations processor from creating an advanced medication delivery program.

13. The medication delivery method of claim 3 wherein the step of creating the advanced delivery program by the advanced program processor further comprises creating an advanced delivery program that comprises delay starts and a series of rate and volume-to-be-infused commands.

14. The medication delivery method of claim 1 further comprising programming the operations processor to provide medication delivery data through the communications system to a PK simulation while the delivery mechanism is under manual user interface control, to use the drug rate delivery information to continue to track and predict the drug concentration even though it is not controlling that rate.

15. The medication delivery method of claim 1 further comprising programming the operations processor to override execution of the advanced delivery program by pressing a stop key at a user interface, at which time the user interface may also be used to program at least one of the delivery rate and delivery volume for manual operation of the delivery mechanism, and to return the delivery mechanism to operation under the advanced delivery program in response to pressing a continue key at the user interface.

16. The medication delivery method of claim 3 wherein the step of creating an advanced medication delivery program in an advanced program processor comprises creating the advanced medication delivery program in an advanced program processor of the AIM wherein the AIM and the medication delivery operations module are located in a same housing.

17. A method for the delivery of medication, the method comprising:

programming an operations processor of a medication delivery operations module, wherein the medication delivery operations module is located in a housing and includes a delivery mechanism having a base function of medication delivery at a selectable rate and a selectable volume, wherein the step of programming comprises programming the operations processor to set the delivery rate and the delivery volume of the base function of the delivery mechanism at fixed values;

further programming the operations processor to control system operations of the delivery operations module, to monitor those operations, and to display error notices on a user interface;

creating an advanced medication delivery program in an advanced program processor that is part of an advanced interface module ("AIM") which is also located in the housing, although the advanced program processor is separate from the operations processor, wherein creating the advanced delivery program comprises assembling a sequence of varying base function operations;

receiving the advanced medication delivery program from the AIM and storing the advanced medication delivery program in a buffer memory, wherein the advanced medication delivery program has a plurality of different values that vary with time for at least one of the delivery rate and the delivery volume;

further programming the operations processor to access the buffer memory for the existence of a complete advanced medication delivery program, and if a complete advanced medication delivery program is found, to execute the advanced delivery program under which the operations processor automatically varies at least one of the rate of delivery and volume of delivery values in accordance with the advanced delivery program autonomously without being under real time control of, or dependent on, any remote processor or data source, including the advanced program processor, or a user interface, except for starting and stopping the operations processor in executing the advanced delivery program, but neither the user interface nor any other control or data device can be used to change the advanced program being executed.

18. The method for the delivery of medication of claim 17, wherein the step of programming the operations processor disables the operations processor from creating an advanced medication delivery program.

19. The method for the delivery of medication of claim 18, further comprising programming the operations processor to provide medication delivery data through the communications system to a PK simulation while the delivery mechanism is under manual user interface control, to use the drug rate delivery information to continue to track and predict the drug concentration even though it is not controlling that rate.

20. A method for the delivery of medication, the method comprising:

programming an operations processor of a medication delivery operations module, wherein the medication delivery operations module is located in a housing and includes a delivery mechanism having a base function of medication delivery at a selectable rate and a selectable volume, wherein the step of programming comprises programming the operations processor to set the delivery rate and the delivery volume of the base function of the delivery mechanism at fixed values, to control system operations of the delivery operations module, and to monitor those operations, and to display error notices on a user interface;

creating an advanced medication delivery program in an advanced program processor that is part of an advanced interface module ("AIM"), wherein the AIM is also located in the housing although the advanced program processor is separate from the operations processor, wherein creating the advanced delivery program comprises assembling a sequence of varying base function operations having a plurality of different values that vary with time for at least one of the delivery rate and the delivery volume;

receiving the advanced medication delivery program and storing the advanced medication delivery program in a buffer memory;

further programming the operations processor to access the buffer memory to determine if a complete advanced medication delivery program exists, and if a complete advanced medication delivery program is found, to execute the advanced delivery program under which the operations processor automatically varies at least one of the rate of delivery and volume of delivery values in accordance with the advanced delivery program autonomously without being under real time control of, or dependent on, any remote processor or data source, including the advanced program processor, or a user interface, except for starting and stopping the operations processor in executing the advanced delivery program, but neither the user interface nor any other control or data device can be used to change the advanced program being executed, wherein the step of programming the operations processor further comprises programming the operations processor to override execution of the advanced medication delivery program by pressing a stop key at the user interface, at which time the user interface may also be used to program at least one of the delivery rate and delivery volume for manual operation of the delivery mechanism, and to return the delivery mechanism to operation under the advanced delivery program in response to pressing a continue key at the user interface.

* * * * *